(12) United States Patent
Resconi (10) Patent No.: US 6,541,584 B1
(45) Date of Patent: Apr. 1, 2003

(54) BIS(TETRAHYDRO-INDENYL) METALLOCENES AS OLEFIN-POLYMERIZATION-CATALYST

(75) Inventor: Luigi Resconi, Ferrara (IT)

(73) Assignee: Basell Poliolefine Italia S.p.A., Milan (IT)

( * ) Notice: Subject to any disclaimer, the term of this patent is extended or adjusted under 35 U.S.C. 154(b) by 0 days.

(21) Appl. No.: 09/600,350

(22) PCT Filed: Nov. 10, 1999

(86) PCT No.: PCT/EP99/08647

§ 371 (c)(1), (2), (4) Date: Jul. 14, 2000

(87) PCT Pub. No.: WO00/29416

PCT Pub. Date: May 25, 2000

(30) Foreign Application Priority Data

Nov. 18, 1998 (EP) .............................. 98203905

(51) Int. Cl.[7] .............................. C07F 7/08; C08F 4/64
(52) U.S. Cl. .................. 526/160; 526/165; 526/943; 585/27; 502/103; 502/104; 502/152
(58) Field of Search ................... 526/160, 165, 526/943; 556/465, 489; 585/27; 502/103, 104, 152

(56) References Cited

U.S. PATENT DOCUMENTS

| | | | | |
|---|---|---|---|---|
| 5,071,808 A | | 12/1991 | Antberg et al. ............ | 502/107 |
| 5,276,208 A | | 1/1994 | Winter et al. ............... | 556/53 |
| 5,948,873 A | * | 9/1999 | Santi et al. | |
| 6,139,484 A | * | 10/2000 | Biagini et al. | |

FOREIGN PATENT DOCUMENTS

| | | | |
|---|---|---|---|
| DE | 4121368 | 1/1993 | |
| EP | 0372414 | 6/1990 | .......... C07F/17/00 |
| EP | 0485821 | 5/1992 | |
| EP | 0485823 | 5/1992 | .......... C07F/17/00 |
| WO | 9411406 | 5/1994 | .......... C07F/17/00 |

OTHER PUBLICATIONS

W. Mengele et al., *ansa–Metallocene Derivatives. 27. Chiral Zirconocene Complexes with Two Dimethylsilylene Bridges*; Organometallics, 12(5)1931–35 (1993).

* cited by examiner

Primary Examiner—Caixia Lu

(57) ABSTRACT

A new class of bridged bis(tetrahydro-indenyl)metallocenes of formula (I),

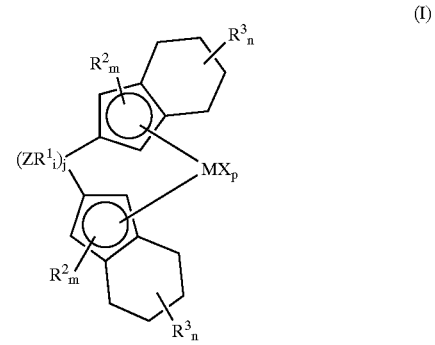

wherein M is Zr or Hf; X are monoanionic sigma ligands; $(ZR^1_i)_j$ is a divalent group bridging the two tetrahydro-indenyl residues; $R^2$ and $R^3$ are halogen, alkyl, cycloalkyl, aryl, alklyaryl or arylalkyl radicals; p is 0–3; i is 1 or 2; j is 1–4; m is 1–2; and n is 0–8. Furthermore, catalysts systems for olefin polymerization containing them are described.

12 Claims, 1 Drawing Sheet

Fig.1

BIS(TETRAHYDRO-INDENYL) METALLOCENES AS OLEFIN-POLYMERIZATION-CATALYST

FIELD OF THE INVENTION

The present invention relates to new bridged bis(tetrahydro-indenyl)metallocenes, to the corresponding ligands and to catalysts for the polymerization of olefins containing them.

PRIOR ART DISCLOSURE

Stereorigid chiral metallocene compounds possessing two bridged cyclopentadienyl groups condensed to a $C_5$–$C_7$ ring are well known in the state of the art and are mainly used as catalytic components in olefin polymerization processes; in particular, metallocene compounds possessing two bridged indenyl or 4,5,6,7-tetrahydro-indenyl groups are widely used in the preparation of stereoregular polyolefins.

The numbering of the substituents on the indenyl group, to which reference is made in the present application, in accordance with the IUPAC nomenclature, is the following:

In the bridged indenyl and tetrahydro-indenyl metallocene compounds known in the state of the art, the indenyl groups are linked together by divalent radicals generally linked to the 1 position of said indenyl groups, and therefore, the common indenyl metallocenes are 1-indenyl compounds.

For example, the European patent application EP 0 485 823 describes a class of bridged bis(1-indenyl)metallocenes, wherein the indenyl groups have a substituent other than hydrogen in the 2 position and are bridged in the 1 position by means of a bridge containing 1 or more carbon atoms (e.g. an ethylene or isopropylidene group) or containing heteroatoms (e.g. a dimethyl-silyl or a diphenyl-silyl group).

European patent application EP 0 485 821 describes a class of bridged bis(4,5,6,7-tetrahydro-inden-1-yl) metallocenes, bearing a substituent in the 2 position and bridged in the 1 position by means of an ethylene, isopropylidene, dimethyl-silyl or diphenyl-silyl group.

The European patent application EP 0 372 414 describes a very broad class of bridged or unbridged metallocenes; among the many metallocenes exemplified, two specific bis-indenyl metallocene compounds are reported, wherein the ethylene group bridging the indenyl groups is linked to the 1 position of one indenyl group and to the 2 position of the other indenyl group (formulae II-1 and II-2, on page 5 of said application). No tetrahydro-indenyl derivatives are mentioned.

The International patent application WO 94/11406 describes a very broad class of metallocene compounds of formula R'Ind—M—(Cp)$Q_k$, wherein: Ind is an indenyl group; R' is a substituent, other than hydrogen, linked in the 2 position of said indenyl group; Cp is a cyclopentadienyl group; M is a transition metal belonging to group 3, 4, 5 or 6 of the Periodic Table of Elements; and Q is a sigma-ligand of the metal M, k being an integer linked to the valence of M. Among the huge plethora of embodiments envisaged in the reported general formula, R' can form a bridge between the 2 position of the Ind group and the Cp group of the above formula. Even in this document, there is no reference to tetrahydro-indenyl derivatives. Moreover, the bis-indenyl zirconocenes tested in the working examples shows very poor activities in ethylene (co)polymerization, leading to products with unsatisfactory molecular weights.

SUMMARY OF THE INVENTION

The Applicant has now unexpectedly found a new class of metallocenes, particularly active as catalyst components for the polymerization of olefins; said metallocenes are characterized by the presence of two 4,5,6,7-tetrahydro-indenyl groups linked in the 2 position by means of a divalent bridging group. Therefore, an object of the present invention is a bridged bis(tetrahydro-indenyl)metallocene of formula (I):

wherein:

M is a transition metal belonging to group 3, 4, 5, 6 or to the lanthanide or actinide groups of the Periodic Table of the Elements (new IUPAC notation);

the substituents X, the same or different from each other, are monoanionic sigma ligands selected from the group consisting of hydrogen, halogen, —R, —OR, —OSO$_2$CF$_3$, —OCOR, —SR, —NR$_2$ and —PR$_2$ groups, wherein the R substituents are linear or branched, saturated or unsaturated, $C_1$–$C_{10}$ alkyl, $C_6$–$C_{20}$ cycloalkyl, $C_6$–$C_{10}$ aryl, $C_7$–$C_{20}$ alkylaryl or $C_7$–$C_{20}$ arylalkyl radicals, optionally containing one or more atoms belonging to groups 13–17 of the Periodic Table of the Elements (new IUPAC notation), such as B, N, P, Al, Si, Ge, O, S and F atoms, and two R substituents may form a 5–7-membered ring; preferably, the substituents X are the same;

(ZR$^1_i$)$_j$ is a divalent group bridging the two tetrahydro-indenyl residues, Z being selected from the group consisting of C, Si, Ge, N and P; the substituents R$^1$, the same or different from each other, are selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing one or more atoms belonging to groups 13–17 of the Periodic Table of the Elements (new IUPAC notation), such as B, N, P, Al, Si, Ge, O, S and F atoms;

the substituents R$^2$ and R$^3$, the same or different from each other, are selected from the group consisting of halogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing one or more atoms belonging to groups 13–17 of the Periodic Table of the Elements (new IUPAC notation; such as B, N, P, Al, Si, Ge, O, S and F atoms), —OR, —SR, —NR$_2$, N-pyrrolyl, N-indolyl, —PR$_2$, —BR$_2$ and —SiR$_3$ groups, wherein the R substituents have the meaning reported above; or two adjacent R$^3$ substituents form a ring having from 4 to 8 carbon atoms;

p is an integer ranging from 0 to 3, being equal to the oxidation state of the metal M minus 2;

i is 1 or 2; j is an integer ranging from 1 to 4; m is an integer ranging from 0 to 2; n is an integer ranging from 0 to 8.

Another object of the present invention is a catalyst for the polymerization of olefins comprising the product obtainable by contacting:

(A) one or more bridged bis(tetrahydro-indenyl) metallocene of formula (I), as described above; and (B) a suitable activating cocatalyst.

Furthermore, the present invention provides a process for the polymerization of olefins comprising the polymerization reaction of one or more olefinic monomers in the presence of a catalyst as described above.

It is another object of the present invention a ligand of formula (II):

(II)

or a double bond isomer thereof, wherein the double bonds of the cyclopentadienyl rings can be in any of the allowed positions, Z, R$^1$, R$^2$, R$^3$, i, j, m and n having the meaning reported above, with the proviso that, when m is 0, then n is different from 0.

DETAILED DESCRIPTION OF THE INVENTION

The bridged bis(tetrahydro-indenyl)metallocenes of formula (I), the catalysts for the polymerization of olefins containing them and the ligands of formula (II), according to the present invention, will be better described in the following detailed description.

It is an object of the present invention a bridged bis (tetrahydro-indenyl)metallocene of formula (I), as reported above, wherein the metal M preferably belongs to group 4 of the Periodic Table of the Elements, and more preferably is Zr or Hf.

The X substituents are preferably Cl, Br or methyl, and are preferably the same.

The divalent bridge (ZR$^1_i$)$_j$ is preferably selected from the group consisting of CR$^1_2$, SiR$^1_2$, GeR$^1_2$, NR$^1$, PR$^1$ and (CR$^1_2$)$_2$, R$^1$ having the meaning reported above. More preferably, said divalent bridge is Si(CH$_3$)$_2$, SiPh$_2$, CH$_2$, (CH$_2$), or C(CH$_3$)$_2$, and even more preferably it is CH$_2$. The variable i is 1 or 2, and more specifically it is 1 when Z is N or P, and it is 2 when Z is C, Si or Ge; j ranges from 1 to 4 and, when j>1, the atoms Z can be the same or different from each other, such as in the divalent bridges —CH$_2$— Si(CH$_3$)$_2$—, —CH$_2$—O— and —CH$_2$—S—.

R$^2$ is preferably selected from the group consisting of methyl, ethyl, n-propyl, i-propyl, n-butyl, t-butyl, phenyl, benzyl and trimethyl-silyl. The choice of the preferred R$^2$ depends also on the nature of the final polymer, as will be evident from what reported below.

R$^3$ is preferably selected form the group consisting of halogen, methyl, ethyl, n-propyl, i-propyl, n-butyl, t-butyl, phenyl and benzyl.

The variable m ranges from 0 to 2; the variable n ranges from 0 or 8.

Non-limiting examples of bridged bis(tetrahydro-indenyl) metallocenes corresponding to formula (I), according to the present invention are:

rac- and meso-methylene-bis(1-methyl-4,5,6,7-tetrahydroinden-2-yl)zirconium dichloride, rac- and meso-methylene-bis(1-ethyl-4,5,6,7-tetrahydroinden-2-yl)zirconium dichloride, rac-methylene-bis(1-t-butyl-4,5,6,7-tetrahydroinden-2-yl)zirconium dichloride, rac- and meso-methylene-bis(1-trimethylsilyl-4,5,6,7-tetrahydroinden-2-yl)zirconium dichloride, rac- and meso-methylene-bis(1-phenyl-4,5,6,7-tetrahydroinden-2-yl)zirconium dichloride, rac- and meso-isopropylidene-bis(1-methyl-4,5,6,7-tetrahydroinden-2-yl)zirconium dichloride, rac- and meso-isopropylidene-bis(1-ethyl-4,5,6,7-tetrahydroinden-2-yl)zirconium dichloride, rac-isopropylidene-bis(1-t-butyl-4,5,6,7-tetrahydroinden-2-yl)zirconium dichloride, rac- and meso-isopropylidene-bis(1-trimethylsilyl-4,5,6,7-tetrahydroinden-2-yl)zirconium dichloride, rac- and meso-isopropylidene-bis(1-phenyl-4,5,6,7-tetrahydroinden-2-yl)zirconium dichloride, rac- and meso-dimethylsilyl-bis(1-methyl-4,5,6,7-tetrahydroinden-2-yl)zirconium dichloride, rac- and meso-dimethylsilyl-bis(1-ethyl-4,5,6,7-tetrahydroinden-2-yl)zirconium dichloride, rac-dimethylsilyl-bis(1-t-butyl-4,5,6,7-tetrahydroinden-2yl)zirconium dichloride, rac- and meso-dimethylsilyl-bis(1-trimethylsilyl-4,5,6,7-tetrahydroinden-2-yl)zirconium dichloride, rac- and meso-dimethylsilyl-bis(1-phenyl-4,5,6,7-tetrahydroinden-2-yl)zirconium dichloride, rac- and meso-ethylene-bis(1-methyl-4,5,6,7-tetrahydroinden-2-yl)zirconium dichloride, rac- and meso-ethylene-bis(1-ethyl-4,5,6,7-tetrahydroinden-2-yl)zirconium dichloride, rac- ethylene-bis(1-t-butyl-4,5,6,7-tetrahydroinden-2-yl) zirconium dichloride, rac- and meso-ethylene-bis(1-trimethylsilyl-4,5,6,7-tetrahydroinden-2-yl)zirconium dichloride, rac- and meso-ethylene-bis(1-phenyl-4,5,6,7-tetrahydroinden-2-yl)zirconium dichloride, methylene-bis(1,3-dimethyl-4,5,6,7-tetrahydroinden-2yl)
zirconium dichloride, methylene-bis(4,7-dimethyl-4,5,6,7-tetrahydroinden-2-yl)zirconium dichloride, rac- and meso-methylene-bis(4-phenyl-4,5,6,7-tetrahydroinden-2-yl)zirconium dichloride, rac- and meso-methylene-bis(4-terbutyl-7-methyl-4,5,6, 7-tetrahydroinden-2-yl)zirconium dichloride, and the corresponding zirconium dimethyl metallocenes.

The bridged bis(tetrahydro-indenyl)metallocenes of formula (I) can be prepared by reaction of the corresponding ligands of formula (II) first with a compound capable of forming a delocalized anion on the cyclopentadienyl ring, and then with a compound of formula $MX_{p+2}$, wherein M, X and p are defined as above, according to common procedures known in the state of the art.

When, in the metallocene of formula (I), one or more X groups are other than halogen, it is necessary to substitute one or more halogens Z of the metallocene halide, obtained as reported above, with one or more substituents X other than halogen. The substitution reaction can be carried out by standard procedures, for example, when the substituents X are alkyl groups, by reacting the metallocene halide with alkylmagnesium halides (Grignard reagents) or with alkyl-lithium compounds.

According to another embodiment, when in formula (I) the X groups have the meaning of —R, as defined above, the methylene-bridged metallocenes of the invention can be obtained by reacting directly a ligand of formula (II) with at least one molar equivalent of a compound of formula $MX_s$, in the presence of at least (p+2) molar equivalents of a suitable alkylating agent, wherein R, M and X have the meaning reported above and s is an integer corresponding to the oxidation state of the metal M and ranges from 3 to 6. Said alkylating agent can be an alkaline or alkaline-earth metal, such as LiR or $MgR_2$, or a Grignard reagent, such as RMgCl or RMgBr, as described in WO 99/36427 (priority European app. no. 98200077.0), in the name of the same Applicant.

According to a preferred embodiment, the bridged bis (tetrahydro-indenyl)metallocenes of formula (I) are prepared by hydrogenation of the corresponding bis-indenyl metallocenes. The hydrogenation of bis-indenyl metallocenes to the corresponding tetrahydro-indenyl derivatives is preferably carried out in organic solvents, such as $CH_2Cl_2$ or DME, at a temperature of 20–70° C, under a $H_2$ pressure of 1–200 bar, for a period ranging from 15 minutes to 24 hours, in the presence of a hydrogenation catalyst, such as Pt, $PtO_2$, Pd or other catalysts known in the state of the art.

The bis-indenyl metallocenes can be prepared from the corresponding bis-indenyl ligands, according to procedures known in the state of the art.

When the divalent bridge $(ZR^1_i)_j$ is —$CH_2$—, the corresponding bis-indenyl ligands can be prepared by reacting formaldehyde with an indene of formula (IV):

(IV)

wherein the $R^2$; $R^3$ have the meaning reported above, n ranges from 0 to 4, and q is 0 or 1, as described in the co-pending European app. No. 98203906.7, in the name of the same Applicant. When the divalent bridge $(ZR^1_i)_j$ is —$CH_2CH_2$—, the corresponding bis-indenyl ligands can be prepared as described in EP 0 942 011 (priority European app. no. 98200728.8), in the name of the same Applicant.

When the divalent bridge $(ZR^1_i)_j$ is $Me_2Si<$, the corresponding bis-indenyl ligands can be prepared by reacting the lithium salt of 4,5,6,7-tetrahydroindene with dimethyldichlorosilane, according to methods known in the state of the art (W. Mengele et al., *Organometallics*, 12:1931–1935, 1993).

It is another object of the invention a ligand having formula (II) as reported above. Said ligands can be prepared by reacting an indene of formula (III):

(III)

or a double bond isomer thereof, wherein the double bonds of the cyclopentadienyl rings can be in any of the allowed positions, the variables $R^2$, $R^3$ and n having the meaning reported above and q being 0 or 1, with a suitable base so to produce the corresponding anion, and then reacting said anion with $(ZR^1_i)_jX'_2$, wherein $(ZR^1_i)_j$ has the meaning reported above and X' is halogen. For instance, when $(ZR^1_i)_j$ is $Me_2Si<$, the procedure described by W. Mengele et al. (*Organometallics*, 12:1931–1935, 1993) can be followed.

When in the ligand of formula (II) m is ≠0, the substituents $R^2$ can also be introduced on the cyclopentadienyl ring by reacting the corresponding ligand of formula (II) wherein m=0 with a suitable amount of a deprotonating agent R'MgBr, R'MgCl or $R'_kB$, wherein R' can have the same meaning of $R^3$, B is an alkaline or alkaline-earth metal, and k is 1 or 2, and then with a suitable amount of an alkylating agent $R^2X'$, wherein $R^2$ has the meaning reported above and X' is halogen.

The bridged bis(tetrahydro-indenyl)metallocenes according to the present invention can be advantageously used as catalytic components for the polymerization of olefins. Thus, another object of the present invention is a catalyst system for the polymerization of olefins, comprising the product obtainable by contacting:

(A) one or more bridged bis(tetrahydro-indenyl) metallocenes of formula (I), as described above, and (B) a suitable activating cocatalyst.

Activating cocatalysts suitable as component (B) in the catalysts of the invention are linear, branched or cyclic alumoxanes, containing at least one group of the type:

wherein the substituents $R^4$, the same or different from each other, are a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, $C_7$–$C_{20}$ arylalkyl radicals, optionally containing Si and Ge atoms, or $R^4$ is a group —O—$Al(R^4)_2$. $R^4$ is preferably methyl, ethyl, isobutyl or 2,4,4-trimethyl-pentyl.

Examples of alumoxanes suitable as activating cocatalysts in the catalysts according to the present invention are methylalumoxane (MAO), tetra-isobutyl-alumoxane (TIBAO), tetra-2,4,4-trimethylpentylalumoxane (TIOAO)

and tetra-2-methyl-pentylalumoxane. Mixtures of different alumoxanes can also be used.

Activating cocatalysts suitable as component (B) in the catalysts of the invention are also the products of the reaction between water and an organometallic aluminum compound, preferably of formula $AlR^5{}_3$ or $Al_2R^5{}_6$, wherein $R^5$ has the meaning reported above. Particularly suitable are the organometallic aluminum compounds of formula (II) described in EP 0 575 875 and those of formula (II) described in WO 96/02580. Moreover, suitable cocatalysts are the ones described in WO 99/21899 (priority European app. no. 97203332.8) and in the European app. no. 99203110.4. Non-limiting examples of organometallic aluminum compounds of formula $AlR^4{}_3$ or $Al_2R^4{}_6$ are: tris (methyl)aluminum, tris(isobutyl)aluminum, tris(isooctyl) aluminum, bis(isobutyl)aluminum hydride, methyl-bis (isobutyl)aluminum, dimethyl(isobutyl)aluminum, tris (isohexyl)aluminum, tris(benzyl)aluminum, tris(tolyl) aluminum, tris(2,4,4-trimethylpentyl)aluminum, bis(2,4,4-trimethylpentyl)aluminum hydride, isobutyl-bis(2-phenyl-propyl)aluminum, diisobutyl-(2-phenyl-propyl)aluminum, isobutyl-bis(2,4,4-trimethyl-pentyl)aluminum. diisobutyl-(2,4,4-trimethyl-pentyl)aluminum, tris(2,3-dimethyl-hexyl) aluminium, tris(2,3,3-trimethyl-butyl)aluminium, tris(2,3-dimethyl-butyl)aluminium, tris(2,3-dimethyl-pentyl) aluminium, tris(2-methyl-3-ethyl-pentyl)aluminium, tris(2-ethyl-3-methyl-butyl)aluminium, tris(2-ethyl-3-methyl-pentyl)aluminium, tris(2-isopropyl-3-methyl-butyl) aluminium and tris(2,4-dimethyl-heptyl)aluminium.

Particularly preferred aluminum compounds are trimethylaluminum (TMA), tris(2,4,4-trimethylpentyl)aluminum (TIOA), triisobutylaluminum (TIBA), tris(2,3,3-trimethyl-butyl)aluminium and tris(2,3-dimethyl-butyl)aluminium.

Mixtures of different organometallic aluminum compounds and/or alumoxanes can also be used.

The molar ratio between aluminum and the metal M of the methylene-bridged metallocene is preferably comprised between about 10:1 and about 50,000:1, and preferably between about 100:1 and about 4,000:1.

In the catalyst system according to the present invention, both said methylene-bridged metallocene and said alumoxane can be pre-reacted with an organometallic aluminum compound of formula $AlR^4{}_3$ or $Al_2R^4{}_6$, wherein the $R^4$ substituents have the meaning reported above.

Further activating cocatalysts suitable as component (B) in the catalysts of the invention are those compounds capable of forming an alkylmetallocene cation; preferably, said compounds have formula $Y^+Z^-$, wherein $Y^+$ is a Broensted acid capable of donating a proton and of reacting irreversibly with a substituent X of the compound of formula (I), and $Z^-$ is a compatible non-coordinating anion, capable of stabilizing the active catalytic species which result from the reaction of the two compounds, and which is sufficiently labile to be displaceable by an olefinic substrate. Preferably, the $Z^-$ anion comprises one or more boron atoms. More preferably, the anion $Z^-$ is an anion of formula $BAr_4{}^{(-)}$, wherein the Ar substituents, the same or different from each other, are aryl radicals such as phenyl, pentafluorophenyl, bis(trifluoromethyl)phenyl. Tetrakis-pentafluorophenyl-borate is particularly preferred. Moreover, compounds of formula $BAr_3$ can be conveniently used.

The catalysts of the present invention can also be used on inert supports. This is achieved by depositing the methylene-bridged metallocene (A), or the product of its reaction with the activating cocatalyst (B), or the component (B) and then the metallocene (A), on a suitable inert support, such as silica, alumina, magnesium halides, olefin polymers or prepolymers, such as polyethylenes, polypropylenes or styrene-divinylbenzene copolymers.

The thus obtained supported catalyst system, optionally in the presence of alkylaluminum compounds, either untreated or pre-reacted with water, can be usefully employed in gas-phase polymerization processes.

The present invention also provides a process for the homo or copolymerization of olefins, comprising the polymerization reaction of one or more olefinic monomers in the presence of a catalyst system as described above. Representative examples of olefinic monomers which may be used in the polymerization process of the invention are ethylene alpha-olefins such as propylene, 1-butene, 1-hexene, 4-methyl-1-pentene and 1-octene, and non-conjugated diolefins such as 1,5-hexadiene.

The catalyst systems of the invention are particularly advantageous in ethylene and propylene homopolymerizations; in fact, by changing the substitution patterns of the bridged bis(tetrahydro-indenyl)metallocenes of the invention it is possible to obtain in high yields, at temperatures of industrial interest, polyethylenes and polypropylenes having intrinsic viscosity (I.V.) ranging from very low to high values. Therefore, an advantage of the metallocenes of the invention is that they allow polymers having a wide range of molecular weights to be obtained. From propylene homopolymerization, by using the metallocenes of formula (I) wherein M is Zr, according to the invention, it is possible to obtain atactic propylene oligomers, terminated with vinylidene end-groups, which are particularly useful as lubricants, functionalizable monomers and chemical intermediates. By using the metallocenes of formula (I) wherein M is Hf, atactic polypropylene having higher molecular weight values are obtainable.

From ethylene homopolymerization, it is possible to obtain linear α-olefins having a Pn (Number Average Degree of Polymerization) ranging from 50 to 500, and preferably from 80 to 350; these α-olefins have more than 90% of terminal vinyl unsaturations (on the total number of terminal vinyl and vinylidene unsaturations). By varying the substitution pattern on the catalysts according to the invention, and in particular by using methylene-bridged bis(1-methyl-4,5,6,7-tetrahydro-inden-2-yl)metallocenes, it is possible to obtain linear α-olefins having a percentage of terminal vinyl unsaturations $\geq 95\%$, preferably $\geq 98\%$, thus providing useful α-olefinic PE waxes. Said α-olefins are linear, having a number of total branches preferably lower than 1/100 carbon atoms, and more preferably lower than 0.1/100C. These α-olefins are particularly useful as polymerization monomers and chemical intermediates.

Moreover, the catalyst systems of the invention are particularly advantageous in the copolymerization of ethylene and propylene, because they allow to obtain copolymers in high yields, having a broad range of comonomer content (ranging from 5 to 70% wt.), having I.V. values ranging 0.6 to 4 dl/g.

The polymerization process can be carried out in the liquid phase, optionally in the presence of inert hydrocarbon solvents, or in the gas phase. The hydrocarbon solvent can be either aromatic, such as toluene, or aliphatic, such as propane, hexane, heptane, isobutane and cyclohexane.

The polymerization temperature is generally comprised between −100° C. and +150° C., and more particularly between 50° C. and 100° C. The lower is the polymerization temperature, the higher are the molecular weights of the polymers obtained.

The molecular weight of the polymers can be further varied by changing the type or the concentration of the catalytic components or by using molecular weight regulators, for example hydrogen.

The molecular weight distribution can be varied by using mixtures of different metallocenes, or by carrying out the polymerization in several steps, that differ with respect to the temperatures of polymerization and/or the concentrations of molecular weight regulators.

An advantageous embodiment of the process for the polymerization of olefins, according to the present invention, is the use of a metallocene of formula (I) in combination with other metallocenes known in the state of the art, in order to produce polyethylenes with a well-defined bimodal distribution. More specifically, a metallocene of formula (I) able to produce PE waxes having low molecular weight, such as methylene-bis(1-methyl-2-tetrahydro-indenyl)metallocenes, may be used in mixture with one or more metallocenes known in the state of the art, able to yield polyethylenes having high molecular weights; by combining the above metallocenes, it is possible to obtain bimodal or multimodal polyethylenes which, despite the presence of the PE wax fraction of the invention (having very low molecular weight), do not have significant amounts of extractables.

The polymerization yields depend on the purity of the metallocene compound of the catalyst.

The metallocene compounds obtained by the process of the invention can be used as they are, or they can undergo purification treatments.

The components of the catalyst can be brought into contact with each other prior to polymerization. The duration of contact is generally between 1 and 60 minutes, preferably between 5 and 20 minutes. The pre-contact concentrations for the metallocene component (A) are between 1 and $10^{-8}$ mole/l, whereas for component (B) they are between 10 and $10^{-8}$ mole/l. Precontact is generally effected in the presence of a hydrocarbon solvent and, if suitable, in the presence of small amounts of monomer.

The following experimental examples are given for illustrative and not limiting purposes.

General Procedures and Characterizations

All operations were performed under nitrogen by using conventional Schlenk-line techniques. Solvents were purified by degassing with $N_2$ and passing over activated (8 hours, $N_2$ purge, 300° C.) $Al_2O_3$, and stored under nitrogen.

The metallocenes and the ligands thereof were characterized by the following methods:

$^1$H-NMR

All compounds were analyzed on an AC 200 Bruker spectrometer by $^1$H NMR ($CDCl_3$, referenced against the peak of residual $CHCl_3$ at 7.25 ppm, or $CD_2Cl_2$, referenced against the peak of residual $CHDCl_2$ at 5.35 ppm). All NMR solvents were dried over $LiAlH_4$, $P_2O_5$ or $CaH_2$ and distilled before use. Preparation of the samples was carried out under nitrogen using standard inert atmosphere techniques.

The polymers were characterized by the following methods:

$^{13}$C-NMR

The $^{13}$C-NMR analyses were performed on a Bruker DPX 400 MHz instrument, in tetrachlorodideuteroethane at 130° C.

Pn (Number Average Degree of Polymerization), evaluated by $^1$H-NMR analysis, gives a molecular weight measure for low molecular weight products, assuming one double bond per chain, as described by Resconi et al. (*JACS*, 120:2308–2321, 1998).

Viscosity Measurements

The intrinsic viscosity (I.V.) was measured in tetrahydronaphtalene (THN) at 135° C.

The polymer molecular weights were determined from the viscosity values.

IR Analysis

IR analysis were performed on a Nicolet 20 instrument, on samples of 0.1 mm thickness.

DSC Analysis

The $T_g$ values were measured on a DSC Mettler instrument. The samples were first heated to 200° C. at 20° C./min. then cooled to −120° C. at 60° C./min. and finally heated to 200° C. at 20° C./min.

Catalyst Components

Methylalumoxane (MAO)

(1) A commercial (Witco, MW 1400) 10% w/w toluene solution of MAO (1.7M) was used as such.

(2) Alternatively, the commercial sample was dried in vacuum to a free-flowing powder (residual $AlMe_3$ about 3–5 mol %).

tris(2,4,4-Trimethyl-pentyl)aluminoxane (TIOAO)

tris(2,4,4-trimethyl-pentyl)aluminum (TIOA) was purchased from Witco and was diluted to a 1M solution in hexane. 3.45 ml of said solution were added at room temperature to 5 ml of toluene, previously deoxygenated and distilled over triisobutylaluminum. 0.031 ml of $H_2O$ were then added at room temperature with a syringe and the resulting solution was stirred for 10 minutes at room temperature.

Catalyst Mixture

The catalyst mixture was prepared by adding the desired amount of the metallocene to the proper amount of MAO, thus obtaining a solution which was stirred for 10 minutes at room temperature and then injected into the autoclave, at the polymerization temperature, in the presence of the monomer.

METALLOCENE SYNTHESIS

Synthesis 1 rac-Methylene-bis(1-methyl-4,5,6,7-tetrahydroinden-2yl)zirconium Dichloride (a) Synthesis of bis(3-Methyl-2-indenyl)methane In a 500 mL flask equipped with magnetic stirring bar were introduced 14.8 g (0.114 moles) of 3-methyl-indene, 2.3 g (0.077 moles) of para-formaldehyde and 4.37 g (0.023 moles) of para-toluenesulphonic acid in 200 ml of toluene; the mixture was heated to 80° C. and was maintained under stirring for 1 hour at 80° C. Then the reaction was quenched with water/$NaHCO_3$; the organic layer was separated, washed with water and brought to dryness under reduced pressure. The crude product was crystallized upon standing at room temperature, and then was further purified by washing with pentane or MeOH, thus isolating 15.5 g of bis(3-methyl-2-indenyl)methane (purity of 89.8% by G.C.; yield=89.8%).

The results of the $^1$H-NMR analysis correspond to the ones reported above.

$^1$H NMR ($CDCl_3$): δ 7.2–7.5 (m, 8H); 3.73 (s, 2H); 3.35 (s, 4H); 2.29 (s, 6H).

(b) Synthesis of rac-Methylene-bis(1-methyl-2-indenyl) zirconium Dichloride 6.5 g of bis(3-methyl-2-indenyl)methane (purity 90% by G.C., 21.5 mmol), obtained as reported above, were dissolved in 160 mL $Et_2O$, in a Schlenk tube with magnetic stirring bar; the solution was cooled to −20° C. and 27 mL of a 1.6 M solution of BuLi in hexane (43.2 mmol) were added dropwise in 15 minutes. The obtained solution was allowed to warm to room temperature and stirred for 5 hours, obtaining a red suspension, which was then cooled to −80° C. and added to a slurry of 5 g of $ZrCl_4$ (MW =233.03, 21.4 mmol) in 160 mL of pentane, in a 500 mL flask, at −80° C. After warming to room temperature, the mixture was stirred overnight. The yellow suspension was dried to a free-flowing powder; said powder was then washed with pentane ($^1$H-NMR analysis showed the presence of both rac- and meso-$CH_2(1$-Me-2-Ind$)_2ZrCl_2$), transferred into an extraction apparatus and finally extracted with refluxing $CH_2C_2$; a yellow precipitate formed in the collecting flask during the extraction. At the end of the extraction, $CH_2Cl_2$ was concentrated to 20 mL and filtered. The residue was washed with $Et_2O$ and pentane, and finally dried, to yield 2.98 g of yellow solid.

$^1$H NMR analysis showed the presence of the pure target product rac-$CH_2(1$-Me-2-Ind$)_2ZrCl_2$. $^1$H NMR ($CD_2Cl_2$, ref. $CDHCl_2$ at 5.383 ppm, room temp.): Cp-$CH_3$, 2.535, s; $CH_2$, 4.375, s; Cp-H, 5.974, s; Ar, 7.2–7.4, m; 7.5–7.6, m.

(c) Synthesis of Methylene-bis(1-methyl-4,5,6,7-tetrahydroinden-2-yl)zirconium Dichloride 0.921 g of rac-$CH_2(1$-Me-2-Ind$)_2ZrCl_2$, obtained as reported above, 150 mg of $PtO_2$ and 80 mL of $CH_2Cl_2$ were placed in a 250 mL glass reactor with a magnetic stirring bar; nitrogen was purged with $H_2$ and the reactor was pressurized to 5.5 atm with $H_2$. The mixture was stirred at room temperature for 3 hours; the pressure was then released and the slurry was filtered to remove $PtO_2$. The obtained residue was washed twice with $CH_2Cl_2$; the yellow-green solution of the filtrate, combined with the washings, was concentrated in vacuo to give a foamy residue, which was then treated with $Et_2O$ (5 mL), filtered and dried, to give 0.30 g of the target product, in the form of a green-gray powder (yield 32.4%).

$^1$H NMR ($CD_2Cl_2$, ref. $CDHCl_2$ at 5.377 ppm, room temp.): Cp-$CH_3$, 1.857, s; $H_4$Ind, 1.6–1.8, m, 2.3–2.6, m, 2.7–3.0, m; $CH_2$, 4.061, s; Cp-H, 5.057, s.

Synthesis 2

Methylene-bis(1-t-butyl-4,5,6,7-tetrahydroinden-2-yl)zirconium Dichloride (a) Synthesis of bis(3-t-Butyl-2-indenyl)methane In a 500 mL flask equipped with magnetic stirring bar were introduced 12.35 g (0.072 moles) of 1-1-butyl-indene, 1.43 g (0.048 moles) of para-formaldehyde and 2.73 g (0.014 moles) of para-toluenesulphonic acid in 200 ml of toluene; the mixture was heated to 80° C. and was maintained under stirring for 6 hours at 80° C. Then the reaction was quenched with water/$NaHCO_3$; the organic layer was separated, washed with water and brought to dryness under reduced pressure. The crude product crystallized upon standing at room temperature, and then was further purified by washing with MeOH, thus isolating 10.8 g bis(3-t-butyl-2-indenyl)methane (purity of 90.9 by G.C.; yield=76.81%).

$^1$H NMR ($CDCl_3$): δ 7.6–7.8 (d, 2H); 7.1–7.4 (m, 6H); 4.23 (s, 2H); 3.34 (s, 4H); 1.58 (s, 18H).

(b) Synthesis of Methylene-bis(1-t-butyl-2-indenyl) zirconium Dichloride 3 g of bis(3-t-butyl-2-indenyl)methane (purity 93.1% by G.C., 7.83 mmol), obtained as reported above, were dissolved in 63 mL $Et_2O$, in a Schlenk tube with magnetic stirring bar; the solution was cooled to −80° C. and 10.6 mL of a 1.6 M solution of BuLi in hexane (16.96 mmol) were added dropwise in 15 minutes. The obtained solution was allowed to warm to room temperature and stirred for 5 hours, thus obtaining a red suspension, which was then cooled to −80° C. and added to a slurry of 1.96 g of $ZrCl_4$ (8.41 mmol), in 63 mL of pentane, in a 250 mL flask, at −80° C. After warming to room temperature, the mixture was stirred overnight. The yellow suspension was dried to a free-flowing powder. $^1$H NMR analysis showed the presence of the target product rac-$CH_2(1$-t-Bu-2-Ind$)_2ZrCl_2$ as the only isomer. The powder was slurried in 100 mL of $CH_2Cl_2$, transferred into an extraction apparatus and extracted with refluxing $CH_2Cl_2$ for 6 hours (a yellow precipitate formed in the collecting flask during the extraction). At the end of the extraction, $CH_2Cl_2$ was concentrated to 10 mL and then filtered. The residue was washed with pentane, until the washing was colorless, and was dried to yield 1.757 g of a yellow solid. $^1$H NMR analysis showed the presence of the pure target product rac-$CH_2(1$-1-Bu-2-Ind$)_2ZrCl_2$.

$^1$H NMR ($CD_2Cl_2$, ref. $CDHCl_2$ at 5.377 ppm, room temp.): t-Bu, 1.719, s; $CH_2$, 4.926, s; Cp-H, 6.220, s; Ar, 7.2–7.3, m; 7.4–7.5, m, 7.8–7.9, m.

Additional 0.4 g of product were recovered from the filtrate, by recrystallization from toluene and washing with $Et_2O$. The combined yield was 55%.

(c) Synthesis of Methylene-bis(1-butyl-4,5,6,7-tetrahydroinden-2-yl)zirconium Dichloride 1.08 g of rac-$CH_2(1$-1-Bu-2-Ind$)_2ZrCl_2$, obtained as reported above, 150 mg of PtO, and 100 mL of $CH_2Cl_2$ were placed in a 250 mL glass reactor with a magnetic stirring bar; nitrogen was purged with $H_2$ and the reactor was pressurized to 5.5 atm with $H_2$. The obtained mixture was stirred at room temperature for 3 hours; the pressure was then released and the slurry was filtered to remove $PtO_2$. The obtained residue was washed twice with $CH_2Cl_2$; the yellow-green solution of the filtrate, combined with the washings, was concentrated in vacuo to give a green foamy residue, which was then treated with $Et_2O$ (5 mL), filtered and dried, to give 0.26 g of the target product, in the form of a light green powder (yield 24%).

$^1$H NMR ($CD_2Cl_2$, ref. $CDHCl_2$ at 5.377 ppm, room temp.): Cp-$CH_3$, 1.376, s; $H_4$Ind, 1.6–1.9, m, 2.4–2.6, m, 2.7–2.9, m, 2.9–3.1, m; $CH_2$, 4.627, s; Cp-H, 5.382, s.

Polymerization Tests

EXAMPLES 1–2 AND COMPARATIVE EXAMPLE 1

Propylene Homopolymerization

Propylene was charged at room temperature in a 1-L or 4.25-L jacketed stainless-steel autoclave, equipped with magnetically driven stirrer and a 35-ml stainless-steel vial, connected to a thermostat for temperature control, previously purified by washing with a $AliBu_3$ solution in hexane and dried at 50° C. in a stream of propylene. $AliBu_3$ (1 mmol in hexane) was added as scavenger before the monomer.

The autoclave was then thermostatted at 2° C. below the polymerization temperature and then a toluene solution containing a mixture of catalyst and cocatalyst, in the amounts reported in Table 1, was injected into the autoclave, by means of nitrogen pressure through the stainless-steel vial. The temperature was rapidly raised to the polymerization temperature and the polymerization was performed at constant temperature for 1 hour.

After having vented the unreacted monomer and having cooled the reactor to room temperature, the polymer was dried under reduced pressure, at 60° C.

The polymerization conditions and the characterization data of the obtained polymers are reported in Table 1; the polymers obtained according to the present invention were all amorphous.

From the obtained results, it is evident that the catalysts containing the bridged (4,5,6,7-tetrahydroinden-2-yl) metallocenes of the present invention are unexpectedly much more active than the corresponding bis-indenyl analogues; the prior art metallocene of Comparative Example 1 turned out to be totally inactive.

EXAMPLES 3 AND 4

Ethylene Homopolymerization

A 1 L stainless-steel autoclave, equipped with magnetic stirrer, temperature indicator and feeding line for the ethylene, was thermostatted with $H_2O$/steam and purified by purging with ethylene at 80° C. Under ethylene purge, 500 mL of n-hexane and TIBA (2 mmol in Ex. 3; 1 mmol in Ex. 4) were added; the temperature was brought to 80° C. and the reactor was vented to remove residual nitrogen. The reactor was then pressurized with ethylene up to 11 bar-a. The catalyst solution, comprising the catalyst and cocatalyst reported in Table 2A, was injected into the autoclave with ethylene overpressure and the ethylene partial pressure was stabilized (Ptot=10 bar-g). Polymerization was carried out at 80° C. for 1 hour, by maintaining a constant ethylene partial pressure of 9.6 bar. The polymerization was interrupted by degassing unreacted ethylene; after filtration and drying in vacuum at 60° C.

The polymerization conditions and results are reported in Table 2A; the characterization data of the obtained polymers are indicated in Table 2B.

From the results reported in Table 2B, it is evident that the metallocenes according to the present invention are able to yield linear α-olefins, having low values of Pn (Number Average Degree of Polymerization) and having a number of terminal vinyl unsaturations up to 100% of the total number of terminal unsaturations. Therefore, by varying the substitution pattern on the catalysts according to the invention, it is possible to obtain linear α-olefins having very high percentage of terminal vinyl unsaturations, thus providing PE waxes having low Pn.

EXAMPLES 5–6 AND COMPARATIVE EXAMPLES 2–3

Ethylene Homopolymerization

A 200 mL glass autoclave, provided with magnetic stirrer, temperature indicator and feeding line for ethylene, was purified and fluxed with ethylene at 35° C. At room temperature were introduced 90 ml of hexane.

The catalytic system was prepared separately in 10 ml of heptane by consecutively introducing the cocatalyst reported in Table 2A and, after 5 minutes under stirring, methylene-bis(1-t-butyl-4,5,6,7-tetrahydroinden-2-yl)zirconium dichloride solved in the lowest possible amount of toluene.

After 5 minutes under stirring, the solution was introduced into the autoclave under ethylene flow; the reactor was closed and the temperature risen to 80° C. The autoclave was then pressurized to 4.6 barg and the total pressure was kept constant by feeding ethylene.

After the polymerization time reported in Table 2A, the reaction was stopped by cooling and degassing the reactor, and by introducing 1 ml MeOH. The obtained polymer was washed with acidic MeOH, the with MeOH and finally dried under vacuum in oven at 60° C.

The polymerization conditions and results are reported in Table 2A; the characterization data of the obtained polymers are indicated in Table 2B.

The polymer obtained in Comparative Example 2 was further characterized by $^{13}$C-NMR analysis; it resulted that said polymer is a linear α-olefin containing 0.15% of $C_2$ branches and 0.09% of $C_{>6}$ branches.

From the results reported in Table 2A, it is evident that the bridged bis(tetrahydro-indenyl)metallocenes according to the present invention are unexpectedly much more active that the bridged bis-indenyl analogues.

The results of Table 2B clearly show that, by changing the substitution pattern of the methylene-bridged metallocenes of the invention, it is possible to obtain in high yields polyethylenes having intrinsic viscosity (I.V.) ranging from very low values to high values, thus allowing polymers having a wide range of molecular weights to be obtained.

EXAMPLES 7–10

Ethylene/Propylene Copolymerization

Copolymerization reactions were carried out in a 1-L jacketed stainless-steel autoclave, as described in Examples 1–2. AliBu$_3$ (1 mmol in hexane) and propylene (530 g, 1 L total volume at 60° C.) were charged and thermostatted at 55° C.; the amounts of catalyst and cocatalyst reported in Table 3 were injected into the autoclave, by means of ethylene pressure (using the amount of ethylene required to achieve the bath composition shown in Table 3), through the stainless-steel vial. The temperature was rapidly raised to 50° C. and the polymerization was carried out for 1 hour, at constant temperature and monomer composition, by feeding the mixture of ethylene and propylene reported in Table 3.

The polymerization was stopped with CO; the unreacted monomers were vented and the obtained copolymer was dried under reduced pressure, at 60° C.

The polymerization conditions and the characterization data of the obtained copolymers are indicated in Table 3.

EXAMPLE 11

Ethylene Homopolymerization

The following polymerization procedure, similar to the one described in examples 3 and 4 was followed: a 1 L stainless-steel autoclave equipped with magnetic stirrer, temperature indicator and feeding line for the ethylene, was thermostatted with $H_2O$/steam and purified by purging with ethylene at 80° C. Under ethylene purge, 500 mL of n-hexane and 1 mmol of TIBA were charged into the reactor; the temperature was brought to 80° C. and the reactor was vented to remove residual nitrogen. The reactor was then pressurized with ethylene up to 11 bar-a. The catalyst solution, comprising the catalyst and cocatalyst reported in Table 2A, was injected into the autoclave with ethylene overpressure and the ethylene partial pressure was stabilized (Ptot=10 bar-g). Polymerization was carried out at 80° C. for 1 hour, by maintaining a constant ethylene partial pressure. The polymerization was interrupted by degassing unreacted ethylene; after filtration and drying in vacuum at 60° C.

Figure 1:
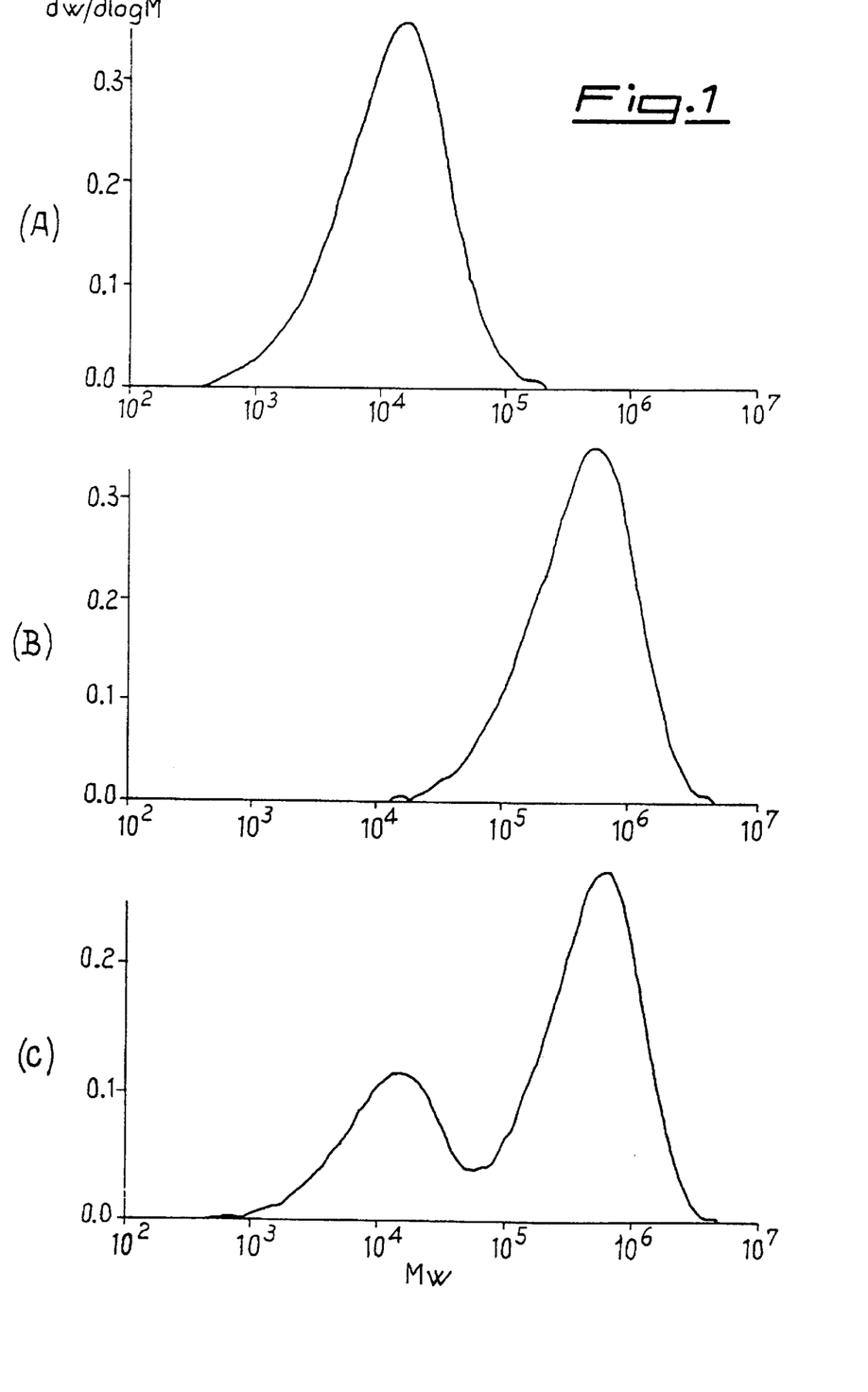
In FIG. 1 are reported the curves obtained by GPC analysis of the polymers of Example 11(A), Comparative Example 4(B) and Example 12(C). Said analysis was carried out with a WATERS 150 instrument, in trichlorobenzene at 135° C.

The polymerization conditions and results are reported in Table 2A; the characterization data of the obtained polymers are indicated in Table 2B and Table 4. The GPC curve of the obtained is reported in FIG. 1A.

From the results reported in Table 2B, it is evident that the metallocenes according to the present invention are able to yield linear α-olefins, having low values of Pn (Number Average Degree of Polymerization) and having a number of terminal vinyl unsaturations up to 100% of the total number of terminal unsaturations.

COMPARATIVE EXAMPLE 4

Ethylene Homopolymerization With a Prior Art Metallocene

The polymerization procedure described in Example 11 was repeated, with the only difference that the catalytic system used was obtained by adding 0.14 ml of MAO solution (1.7M in toluene, 0.24 mmol Al) to 0.25 mg of rac-Me$_2$C(3-iPr-Ind)$_2$ZrCl$_2$ (0.48 μmol) dissolved in 2.5 mL of toluene (Al/Zr=500), and aging the mixture 10 minutes.

The polymerization yielded polyethylene with an activity of 38 kgPE/g$_{cat}$.h; characterization data of the obtained polymer are indicated in Table 4. The GPC curve of the obtained is reported in FIG. 1B.

EXAMPLE 12

Preparation of Bimodal Polyethylene

1 L stainless-steel autoclave, thermostatted with H$_2$O/steam and purified by purging with ethylene at 80° C. Under ethylene purge, 540 mL technical hexane and 1 mmol TIBA were charged into the reactor, the temperature was brought to 80° C. and the reactor was vented to remove residual nitrogen, then pressurized with ethylene up to 9.5 bar-g.

0.17 mL of MAO solution (1.7 M in toluene, 0.28 mmol Al) were added to 0.25 mg of rac-CH$_2$(1-Me-2-H$_4$Ind)$_2$ZrCl$_2$ (0.57 μmol) dissolved in 1.2 mL of toluene (Al/Zr=500) and aged 10 min.

0.14 mL of MAO solution (1.7 M in toluene, 0.24 mmol Al) were added to 0.25 mg of rac-Me$_2$C(3-iPr-Ind)$_2$ZrCl$_2$ (0.48 μmol) dissolved in 2.5 mL of toluene (Al/Zr=500) and aged 10 min.

The two catalyst/cocatalyst mixtures were combined, siphoned into the steel vial and injected into the reactor by means of ethylene overpressure, the ethylene partial pressure was then stabilized to 9.6 bar-a, (P$_{tot}$ 11 bar-a). The test was carried out at 80° C. for 30 min hour, by maintaining a constant ethylene partial pressure. After quenching the reaction with CO and degassing unreacted ethylene, the polymer was isolated by filtration and dried in vacuo at 60° C., thus obtaining 23.5 g of polyethylene, having a solubility in cold xylene of 0.3% wt; characterization data of the obtained polymer are indicated in Table 4. The GPC curve of the obtained is reported in FIG. 1C.

The diagrams reported in FIG. 1 clearly demonstrate that, by combining the metallocene rac-CH$_2$(1-Me-2-H$_4$Ind)$_2$ZrCl$_2$ of the invention, able to give PE waxes, and the prior art metallocene rac-Me$_2$C(3-iPr-Ind)$_2$ZrCl$_2$ able to give PE of higher molecular weight, it is possible to produce polyethylene polymers with a well-defined bimodal distribution.

TABLE 1

Propylene homopolymerization

| Ex. | Metallocene Type | (μmol) | MAO (mmol) | Al/Zr (mol) | T (° C.) | Yield (g) | Activity (kg/gCat.h) | Mw | I.V. (dl/g) |
|---|---|---|---|---|---|---|---|---|---|
| 1 | r-CH$_2$(1-tBut-2-tetrahydro-Ind)$_2$ZrCl$_2$ | 0.38 | (1) 1.14 | 3000 | 50 | 138.01 | 690.1 | 72,000 | 0.7 |
| 2 | r-CH$_2$(1-tBut-2-tetrahydro-Ind)$_2$ZrCl$_2$ | 0.57 | (1) 1.72 | 3000 | 30 | 12.57 | 41.9 | 178,000 | 1.37 |
| Comp. 1 | CH$_2$(2-Ind)$_2$ZrCl$_2$ | 4.94 | (2) 7.41 | 1500 | 50 | 0 | INACTIVE | — | — |

(1) Commercial 10% w/w toluene solution of MAO (1.7M; Witco).
(2) The commercial sample (1) was dried in vacuum to a free-flowing powder (residual AlMe$_3$ about 3–5 mol %).

TABLE 2A

Ethylene homopolymerization

| Example | Metallocene Type | mg | Cocatalyst Type | (mmol) | Al/Zr (mol) | Time (min) | Yield (g) | Activity (Kg/gCat.h) |
|---|---|---|---|---|---|---|---|---|
| 3 | r-CH$_2$(1-Me-2-tetrahydro-Ind)$_2$ZrCl$_2$ | 0.2 | MAO (1) | 0.23 | 500 | 60 | 14.0 | 70.0 |
| 4 | r-CH$_2$(1-t-But-2-tetrahydro-Ind)$_2$ZrCl$_2$ | 0.2 | MAO (1) | 0.86 | 3000 | 60 | 32.1 | 214.0 |
| 5 | r-CH$_2$(1-t-But-2-tetrahydro-Ind)$_2$ZrCl$_2$ | 0.12 | MAO (1) | 0.24 | 1000 | 2 | 1.2 | 1724.6 |
| 6 | r-CH$_2$(1-t-But-2-tetrahydro-Ind)$_2$ZrCl$_2$ | 0.1 | TIOAO | 0.2 | 1000 | 6 | 0.71 | 408.2 |
| 11 | r-CH$_2$(1-Me-2-tetrahydro-Ind)$_2$ZrCl$_2$ | 0.5 | MAO (1) | 0.57 | 500 | 60 | 26.0 | 52.0 |
| Comp. 2 | CH$_2$(2-Ind)$_2$ZrCl$_2$ | 0.3 | MAO (2) | 0.75 | 1000 | 10 | 1.51 | 132.6 |
| Comp. 3 | CH$_2$(2-Ind)$_2$ZrCl$_2$ | 0.5 | TIOAO | 2.50 | 2000 | 30 | 1.54 | 27.1 |

(1) Commercial 10% w/w toluene solution of MAO (1.7M; Witco).
(2) The commercial sample (1) was dried in vacuum to a free-flowing powder (residual AlMe$_3$ about 3–5 mol %).

TABLE 2B

Ethylene homopolymerization

| Example | I.V. (dl/g) | $M_v$ | Pn | ΔH (J/g) | $T_m$ (° C.) | Terminal vinyl unsaturations (%) | Terminal vinylidene unsaturations (%) |
|---|---|---|---|---|---|---|---|
| 3 | 0.42 | 15,800 | 304 | 208 | 140 | 100 | 0 |
| 4 | 4.99 | 480,000 | 8540 | n.d. | n.d. | n.d. | n.d. |
| 5 | 4.42 | 405,300 | n.d. | n.d. | n.d. | n.d. | n.d. |
| 6 | >8 | >900,000 | n.d. | n.d. | n.d. | n.d. | n.d. |
| 11 | 0.41 | 15300 | 304 | 242 | 131 | 100 | 0 |
| Comp. 2 | 0.17 | 4530 | 81 | 217 | 125 | 91.5 | 8.5 |
| Comp. 3 | 0.2 | n.d. | n.d. | n.d. | n.d. | n.d. | n.d. |

TABLE 3

Ethylene/propylene copolymerization

| | Metallocene | | MAO | Al/Zr | $C_3$ bath | $C_2$ bath | $C_3$ feed | $C_2$ feed | Yield | Activity | C2 | I.V. | Tg |
|---|---|---|---|---|---|---|---|---|---|---|---|---|---|
| Ex. | Type | μmol | (mmol) | (mol) | (g) | (g) | (g) | (g) | (g) | (Kg/gCat.h) | (% wt) | (dl/g) | (° C.) |
| 7 | r-CH$_2$(1-t-Bu-2-tetrahydro-Ind)$_2$ZrCl$_2$ | 0.95 | (1) 2.86 | 3000 | 314 | 3.4 | 0.0 | 0.0 | 16.98 | 34.0 | 5.0 | 0.68 | −7 |
| 8 | r-CH$_2$(1-t-Bu-2-tetrahydro-Ind)$_2$ZrCl$_2$ | 0.48 | (1) 1.43 | 3000 | 311 | 6.8 | 0.0 | 20.3 | 63.99 | 255.9 | 11.2 | 1.28 | −24 |
| 9 | r-CH$_2$(1-t-Bu-2-tetrahydro-Ind)$_2$ZrCl$_2$ | 0.38 | (1) 1.14 | 3000 | 294 | 21.7 | 2.7 | 12.8 | 67.61 | 338.1 | 36.6 | 1.61 | −31 |
| 10 | r-CH$_2$(1-t-Bu-2-tetrahydro-Ind)$_2$ZrCl$_2$ | 0.38 | (1) 1.14 | 3000 | 303 | 49.3 | 13.2 | 20.6 | 36.01 | 180.1 | 67.5 | 3.63 | −35 |

(1) Commercial 10% w/w toluene solution of MAO (1.7M; Witco).

TABLE 4

Ethylene homopolymerization

| Example | Metallocene | Activity (Kg/g$_{Cat}$.h) | I.V. (dl/g) | $M_w$ | $M_n$ | $M_w/M_n$ |
|---|---|---|---|---|---|---|
| Comp. 4 | rac-Me$_2$C(3-iPr-Ind)$_2$ZrCl$_2$ | 38.0 | 6.9 | 580,500 | 244,700 | 2.4 |
| 11 | rac-CH$_2$(1-Me-2-H$_4$Ind)$_2$ZrCl$_2$ | 52.0 | 0.41 | 18,000 | 38,900 | 2.8 |
| 12 | rac-Me$_2$C(3-iPr-Ind)$_2$ZrCl$_2$ + rac-CH$_2$(1-Me-2-H$_4$Ind)$_2$ZrCl$_2$ | 94.0 | 4.44 | 433,000 | 23,100 | 18.8 bimodal |

What is claimed is:

1. A bridged bis(tetrahydro-indenyl)metallocene of formula (I):

wherein:

M is a transition metal belonging to group 3, 4, 5, 6 or to the lanthanide or actinide groups of the Periodic Table of the Elements;

the substituents X, the same or different from each other, are monoanionic sigma ligands selected from the group consisting of hydrogen, halogen, —R, —OR, —OSO$_2$CF$_3$, —OCOR, —SR, —NR$_2$ and —PR$_2$ groups, wherein the R substituents are linear or branched, saturated or unsaturated, $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radicals, optionally containing one or more atoms belonging to groups 13–17 of the Periodic Table of the Elements, and two R substituents may form a 5–7 membered ring;

(ZR$^1_i$)$_j$ is a divalent group bridging the two tetrahydro-indenyl residues, Z being selected from the group consisting of C, Si, Ge, N and P; the substituents R$^1$, the same or different from each other, are selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing one or more atoms belonging to groups 13–17 of the Periodic Table of the Elements;

the substituents R$^2$ and R$^3$, the same or different from each other, are selected from the group consisting of halogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing one or more atoms belonging to groups 13–17 of the Periodic Table of the Elements, —OR, —SR, —NR$_2$, N-pyrrolyl, N-indolyl, —PR$_2$, —BR$_2$ and —SiR$_3$ groups, wherein the R substituents have the meaning reported above; or two adjacent R$^3$ substituents form a ring having from 4 to 8 carbon atoms;

p is an integer ranging from 0 to 3, being equal to the oxidation state of the metal M minus 2;

i is 1 or 2;

j is an integer ranging from 1 to 4;

m is an integer ranging from 1 to 2; and n is an integer ranging from 0 to 8.

2. The bridged bis(tetrahydro-indenyl)metallocene according to claim 1, wherein said metal M is Zr or Hf.

3. The bridged bis(tetrahydro-indenyl)metallocene according to claim 1 or 2, wherein said X substituents are Cl, Br or methyl.

4. The bridged bis(tetrahydro-indenyl)metallocene according to claim 1, wherein $(ZR^1_i)_j$ is selected from the group consisting of $CR_2$, $SiR^1_2$, $GeR_2$, $NR^1$, $PR^1$ and $(CR^1_2)_2$.

5. The bridged bis(tetrahydro-indenyl)metallocene according to claim 4, wherein $(ZR^1_i)_j$ is selected from the group consisting of $Si(CH_3)_2$, $SiPh_2$, $CH_2$, $(CH_2)_2$ and $C(CH_3)_2$.

6. The bridged bis(tetrahydro-indenyl)metallocene according to claim 1, wherein $R^2$ is selected from the group consisting of methyl, ethyl, n-propyl, i-propyl, n-butyl, t-butyl, phenyl, benzyl and trimethyl-silyl; and $R^3$ is selected form the group consisting of halogen, methyl, ethyl, n-propyl, i-propyl, n-butyl, t-butyl, phenyl and benzyl.

7. A catalyst for the polymerization of olefins comprising the product obtained by contacting:

(A) one or more bridged bis(tetrahydro-indenyl) metallocenes of formula (I):

(I)

wherein:

M is a transition metal belonging to group 3, 4, 5, 6 or to the lanthanide or actinide groups of the Periodic Table of the Elements;

the substituents X, the same or different from each other, are monoanionic sigma ligands selected from the group consisting of hydrogen, halogen, —R, —OR, —OSO$_2$CF$_3$, —OCOR, —SR, —NR$_2$ and —PR$_2$ groups, wherein the R substituents are linear or branched, saturated or unsaturated, $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radicals, optionally containing one or more atoms belonging to groups 13–17 of the Periodic Table of the Elements, and two R substituents may form a 5–7 membered ring;

$(ZR^1_i)_j$ is a divalent group bridging the two tetrahydro-indenyl residues, Z being selected from the group consisting of C, Si, Ge, N and P; the substituents $R^1$, the same or different from each other, are selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing one or more atoms belonging to groups 13-17 of the Periodic Table of the Elements;

the substituents $R^2$ and $R^3$, the same or different from each other, are selected from the group consisting of halogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing one or more atoms belonging to groups 13–17 of the Periodic Table of the Elements, —OR, —SR, —NR$_2$, N-pyrrolyl, N-indolyl, —PR$_2$, —BR$_2$ and —SiR$_3$ groups, wherein the R substituents have the meaning reported above; or two adjacent $R^3$ substituents form a ring having from 4 to 8 carbon atoms;

p is an integer ranging from 0 to 3, being equal to the oxidation state of the metal M minus 2;

i is 1 or 2;

j is an integer ranging from 1 to 4;

m is an integer ranging from 1 to 2;

n is an integer ranging from 0 to 8; and (B) a suitable activating cocatalyst.

8. The catalyst according to claim 7, wherein said activating cocatalyst is at least one of an alumoxane and a compound that forms an alkylmetallocene cation.

9. A process for the polymerization of olefins comprising the polymerization reaction of one or more olefinic monomers in the presence of a catalyst as described in claim 7 or 8.

10. The process according to claim 9, wherein said olefinic monomer is selected from the group consisting of ethylene, propylene, 1-butene, 1-hexene, 4-methyl-1-pentene, 1-octene and mixtures thereof.

11. The process according to claim 10, for the production of atactic propylene oligomers, terminated with vinylidene end-groups.

12. The process according to claim 10, for the production of ethylene linear α-olefins having Pn ranging from 50 to 500, wherein more than 95% of the unsaturations are terminal vinyl unsaturations.

* * * * *

UNITED STATES PATENT AND TRADEMARK OFFICE
CERTIFICATE OF CORRECTION

PATENT NO. : 6,541,584 B1
DATED : November 10, 1999
INVENTOR(S) : Luigi Resconi It is certified that error appears in the above-identified patent and that said Letters Patent is hereby corrected as shown below:

Column 19,
Line 14, change "$CR_2$, $SiR^1_2$, $GeR_2$" to -- $CR^1_2$, $SiR^1_2$, $GeR^1_2$ --

Signed and Sealed this

Eleventh Day of January, 2005

JON W. DUDAS
*Director of the United States Patent and Trademark Office*